United States Patent [19]

Nath

[11] 3,936,440

[45] Feb. 3, 1976

[54] METHOD OF LABELING COMPLEX METAL CHELATES WITH RADIOACTIVE METAL ISOTOPES

[75] Inventor: Amar Nath, Bala Cynwyd, Pa.

[73] Assignee: Drexel University, Philadelphia, Pa.

[22] Filed: May 22, 1974

[21] Appl. No.: 472,305

[52] U.S. Cl.............................. 260/211.7; 424/201
[51] Int. Cl.$^2$.......................................... C07H 23/00
[58] Field of Search...................... 260/211.7; 424/1

[56] References Cited
UNITED STATES PATENTS 3,505,019    4/1970    Axen et al. ............................. 424/1

*Primary Examiner*—Johnnie R. Brown
*Assistant Examiner*—Cary B. Owens
*Attorney, Agent, or Firm*—Paul & Paul

[57] ABSTRACT

A method is provided for labeling a complex metal chelate with a radioactive metal isotope via isotopic exchange between the metal atom of the complex metal chelate and the radioactive metal isotope. The complex metal chelate, in a suitable redox state, is mixed in solution with a radioactive metal isotope, freeze-dried, exposed to an electron-accepting gas and thereafter subjected to thermal treatment, whereby isotopic exchange occurs and the complex metal chelate is labeled with the radioactive metal isotope. Furthermore, an additional step comprising exposure to an atmosphere of high relative humidity is provided to increase the yield of isotopic exchange.

23 Claims, No Drawings

METHOD OF LABELING COMPLEX METAL CHELATES WITH RADIOACTIVE METAL ISOTOPES

BACKGROUND OF THE INVENTION

A. Field of the Invention

The present invention pertains to the field of complex metal chelate chemistry and, more specifically, to a method whereby complex metal chelates are labeled, or "tagged", with a radioactive metal isotope through a mechanism whereby isotopic exchange occurs between the complex metal chelate and an "activated" radioactive metal isotope.

The labeled complex metal chelate compounds prepared in accordance with the present invention are useful in various applications which utilize the presence of a radioactive isotope in the complex metal chelate compound. One area employing such application is the field of medical diagnosis of pernicious anemia and other malabsorption states. Vitamin $B_{12}$, (hereinafter also referred to as "cyanocobalamin"), is one such complex metal chelate compound which can be labeled with a radioactive metal isotope, such as $^{57}Co^{+2}$, in accordance with the present invention. Vitamin $B_{12}$ is itself useful as a preventative for pernicious anemia and, when labeled with a radioactive isotope, its presence, or absence may be readily detected throughout the body, thus facilitating the diagnosis of abnormalities effecting its use thereby.

Furthermore, various radioactively labeled complex metal chelate compounds are being evaluated as chemotheraputic agents for the localized treatment of cancer by irradiation, for example cancer of the liver. There are other useful medical applications requiring "tagged" complex metal chelate compounds which, by virtue of their radioactivity, can be easily detected, or traced, in living organisms.

B. Description of the Prior Art

Complex metal chelate compounds containing radioactive metal isotopes have been known and utilized in the prior art. For example, "tagged" Vitamin $B_{12}$, that is Vitamin $B_{12}$ containing a radioactive isotope of cobalt, has been used in the diagnosis of pernicious anemia and has been prepared via biochemical synthesis, wherein microbes are cultured in the presence of a cobalt-57 salt and produce Vitamin $B_{12}$ containing cobalt-57 isotopes which must then be purified by lengthy chromotographic separations. However, numerous attempts to label Vitamin $B_{12}$ by isotopic exchange in solution have been unsuccessful; see R. N. Booe, et al., "The Exchange Stability of Cobalt in Vitamin $B_{12}$", 73 *J. Amer. Chem. Soc.* 5446 (1951); and R. A. Baldwin, et al., "The Failure to Crystalline Vitamin $B_{12}$ to Exchange with Cobalt-60 in Acidic and Neutral Aqueous Solutions"; 73 *J. Amer. Chem. Soc.* 4968 (1951).

Isotopic exchange between a radioactive metal isotope in a complex metal chelate takes place in solution only for chelates with labile ligands. In complex metal chelates in which the metal atoms exist in a higher oxidation state, the ligands are very strongly bound to the central metal atoms. However, in complex metal chelates in which the metal exists in a lower redox state, the ligands are more labile, i.e. the cobalt is not as strongly bound to the ligand and theoretically is more susceptible to isotopic exchange with a radioactive metal isotope, provided that sufficient energy is imparted to "activate" the radioactive metal isotope.

For example, in complex Cobalt (III) chelates, the ligands are very strongly bound to the central cobalt atom and, therefore, isotopic exchange is very difficult to achieve. However, complex Cobalt (II) chelates have much more labile ligands and, accordingly, should be much more susceptible to isotopic exchange with an activated radioactive metal isotope. In practice, however, attempts in the past, such as those made by Diehl and Voigt, "The Failure of Exchange Between Vitamin $B_{12r}$ and Radioactive Cobalt Chloride", 32 *Iowa State J. of Science* 4 (1958), have been unsuccessful. Voigt and his co-workers tried unsuccessfully to exchange $^{60}Co^{+2}$ with the central cobalt atom of Vitamin $B_{12r}$ in solution. Apparently, it was thought that the cobalt atom in Vitamin $B_{12r}$ was still too strongly bonded to the ligands for isotopic exchange to occur.

Attempts have also been made to achieve isotopic exchange for complex metal chelates in the solid state. These attempts have met with some success, but have not provided a method of labeling complex metal chelate compounds with a radioactive metal isotope having the advantages of the novel method of the present invention.

One such solid state method was that used by Nath, et al, "Isotopic Exchange in the Solid State and Thermal Annealing of Recoil Damage in cobalt Complexes: A New Model", Vol. 4. No 2 *Indian J. of Chem.* 51–56 (1966), which was unsuccessful in effecting noticeable isotopic exchange in cyanocobalamin. That method involved heating of a mixture of the cyanocobalamin and $^{60}Co^{+2}$ activity to about 180°C in a vacuum. The cobalt complexes which were found to undergo isotopic exchange in the solid state, such as tris-dipyridyl Cobalt (III) perchlorate, were much simpler compounds than the complex metal chelates of the present invention. Furthermore, it was noted that in accordance with the prior art method of Nath et al., the rate of exchange was considerably retarded by the presence of oxygen.

Therefore, while radioactively labeled complex metal chelate compounds had been known in the prior art, the methods used to label these compounds have not been able to satisfactorily supply the compounds efficiently and economically. Furthermore, the prior art methods have been unable to produce many of the labeled complex metal chelate compounds of the present invention.

SUMMARY OF THE INVENTION

In accordance with the present invention, a method is provided for labeling a complex metal chelate with a radioactive metal isotope via isotopic exchange in the solid state between the metal atom of the complex metal chelate and the radioactive metal isotope. The method is comprised of the general steps of; preparation of a solid mixture of a complex metal chelate compound and a radioactive metal isotope dopant, exposure of this mixture to an electronaccepting gas, and then thermal treatment of the mixture in the presence of the electron-accepting gas whereby isotopic exchange occurs and the complex metal chelate compound is labeled with the radioactive metal isotope. Furthermore, an additional step is provided after the thermal treatment comprising exposure of the mixture to an atmosphere of high relative humidity whereby the yield of the isotopic exchange is increased. It should be noted, however, that depending upon the particular complex metal chelate compound being used, it may be necessary to utilize the same in a lower redox state, that is it may be necessary to conduct the labeling of the chelate in its reduced form.

It is, therefore, an object of the present invention to provide a useful method of labeling a complex metal chelate compound with a radioactive metal isotope.

It is further an object of this invention to provide a method of synthesis for complex metal chelate compounds wherein the metal is in the form of a radioactive isotope of the metal.

It is yet a further object of this invention to provide a method for labeling complex metal chelate compounds, whereby isotopic exchange is effected between an activated radioactive metal dopant and a complex metal chelate compound.

It is yet a further object of this invention to provide a method whereby a complex metal chelate compound can be labeled with a radioactive metal isotope, so that the labeled chelate compound can be detected by virtue of its radioactivity.

It is yet a further object of this invention to provide a method of labeling complex metal chelate compounds with a radioactive metal isotope which is, with proper safeguards and precautions, safe to practice and effective to provide a labeled complex metal chelate compound with high specific activity.

Other objects and advantages of these methods of the present invention will be readily apparent to those skilled in the art through the study of the following description of the preferred embodiment and the appended claims.

DESCRIPTION OF THE PREFERRED EMBODIMENT

In accordance with the present invention, any metal chelate compound, including cyanocobalamin, cobaltocene, aquocobalamin, porphyrins, phthalocyanines and other macrocyclic compounds, may be labeled with a radioactive isotope of either the same metal as that present in the complex metal chelate compound or a different metal than that present in the complex metal chelate compound.

For purposes of the present invention, the radioactive metal isotopes are provided in the form of a radioactive metal isotope dopant, which is an ionic compound containing a "carrier-free" metal isotope, that is a compound which contains only the radioactive isotopes of the metal and substantially no non-radioactive isotopes thereof. Therefore, these dopants are said to be of "high specific activity".

Typical of the radioactive metal isotopes which are within the purview of the present invention are $^{57}Co^{+2}$, $^{60}Co^{+2}$, $^{52}Fe^{+2}$, $^{52}Fe^{+3}$, $^{48}Cr^{+3}$, $^{95}Tc^{+4}$, $^{97}Tc^{+4}$ and $^{99}Tc^{+4}$. Of course, it is to be understood that any radioactive isotope of a metal is fully within the purview of the present invention.

The electron-accepting gases which can be utilized in accordance with the present invention include, but are not limited to, oxygen, nitrous oxide, carbon dioxide and sulfur hexafluoride.

Furthermore, it is to be understood that for purposes of the present invention the term "humidity" refers to the presence of vapors of water, as well as other solvents having a dielectric constant approximating that of water.

As will be readily apparent to those skilled in the art, for purposes of the present invention, the designation of metal atoms, or isotopes, as Co (II), for example, refers to a metal atom, or isotope, which is bound in a solid crystalline structure and which will not dissociate in solvent, while the designation as $Co^{+2}$, for example, refers to the ionic form of the atom, or isotope, in a compound which will dissociate into ions of its component parts in solution.

In accordance with the present invention, a mechanism has been proposed for isotopic exchange in the solid state between a complex metal chelate and a radioactive metal isotope ion. In the solid state, electrons, or "holes", which are loosely bound by the crystal defects, in the complex metal chelate are "detrapped", or "released", upon thermal treatment and are free to migrate in the solid. These freely migrating electrons or "holes" are available to interact with the radioactive metal isotope ion to form an electronically excited ion, i.e. an "activated" radioactive metal isotope. This "activated" radioactive metal isotope is very reactive and reacts with the ligand of the complex metal chelate molecule, which contains an inactive non-radioactive cobalt atom. The ligand of the chelate molecule is then transferred onto the activated metal isotope and the inactive metal atom of the chelate is replaced via the mechanism termed "isotopic exchange".

The energy required for this isotopic exchange is therefore, provided by the activated metal isotope ion, which results from the electronic excitation of a radioactive dopant. In accordance with the novel method of the present invention, the "holes" required to activate the radioactive metal isotope are provided by increasing the number of defects in the complex metal chelate compound. This is accomplished by exposure of a mixture of complex metal chelate compound and the radioactive metal isotope dopant to an atmosphere of an electron-accepting gas, such as oxygen and the like.

It has also been found that in the practice of the present invention subjecting the reaction mixture of complex metal chelate compound and radioactive metal isotope dopant in the presence of such an electron-accepting gas to thermal treatment, whereby a mixture is maintained at a temperature of between 100°–300°C for a period of approximately 24–96 hours, increases the rate of isotopic exchange.

Furthermore, it has been found desirable to add an additional optional step after the thermal treatment of the reaction mixture to further increase the yield of the isotopic exchange. This step consists of exposing the reaction mixture to an atmosphere of high relative humidity for at least about 24 hours. It is believed that additional "holes" are freed as a result of the vapors comprising the humidty, such vapors being those of water, or other solvents of high dielectric constants.

In accordance with the present invention, one preferred embodiment provides a method for labeling Vitamin $B_{12}$, that is cyanocobalamin, with $^{57}Co^{+2}$, a radioactive isotope of cobalt. It is to be understood, however, that it is fully within the purview of the present invention to substitute other radioactive isotopes of cobalt, such as $^{60}Co^{+2}$, or radioactive isotopes of other metals within the scope of the present invention.

In the preferred embodiment of the present invention, whereby Vitamin $B_{12}$ is labeled with a radioactive isotope of cobalt, a "specific activity", or the degree of incorporation of the radioactive isotope in the Vitamin $B_{12}$, within the range of about 1 millicurie per milligram (1mc/mg) of Vitamin $B_{12}$ to 200 mc/mg of Vitamin $B_{12}$ can be achieved. This wide range of specific activity is possible, since the degree of incorporation of the radioactive isotope is largely governed by the amount of radioactive cobalt dopant used in the practice of the invention.

Vitamin $B_{12}$ is a very large and complex metal chelate in which cobalt (III) is tightly bound to the ligand in its higher redox state. In accordance with the present invention, a reduced form of Vitamin $B_{12}$, (hereinafter also referred to as "Vitamin $B_{12r}$"), in which the bound cobalt is in the cobalt (II) redox state, is utilized because its ligands are more labile and consequently, require less energy to achieve isotopic exchange.

For purposes of the present invention, it is to be understood that a "reduced complex metal chelate compound" preferably refers to a complex metal chelate compound in its most labile form, usually its lowest redox state, although it also includes all complex metal chelate compounds which exist in only a single redox state. Likewise, any reference to a "higher redox state" refers to a less labile redox state, if one exists, and includes the single redox state of compounds having only a single redox state. In accordance with the preferred embodiment of the present invention, a method of labeling complex cobalt chelate compounds with a radioactive isotope of cobalt is provided. Specifically, Vitamin $B_{12}$ containing a radioactive isotope of cobalt is synthesized by a method comprising the steps of providing an aqueous solution containing Vitamin $B_{12r}$ and a radioactive cobalt isotope dopant, such as $^{57}CoCl_2$, then freeze-drying the solution to form a solid mixture, which is then exposed to an electron-accepting gas, such as oxygen, and, finally, subjected to thermal treatment until isotopic exchange is substantially complete and Vitamin $B_{12r}$ containing $^{57}Co$ (II) is produced. Thereafter, the labeled Vitamin $B_{12r}$ is converted by conventional techniques to labeled Vitamin $B_{12}$.

Parenthetically, it is to be understood that practice of the present invention does not require use of the reduced form of the complex metal chelate, which after being labeled may then be converted to a higher redox state, if desired. Rather, a complex metal chelate may be utilized in any of its potential redox states within the purview of the invention, the choice of redox state merely affecting the rate and yield of reaction depending upon the specific reactants choosen. Of course, where the reduced form of the complex metal chelate is not used in the practice of the method of the present invention, the corresponding conversion of the labeled product to a higher redox state may, or may not, be necessary. In the case of Vitamin $B_{12}$, however, the reduction to Vitamin $B_{12r}$ is necessary.

The reduced form of Vitamin $B_{12}$ is its most labile form. It is within the purview of the invention that the reduction of Vitamin $B_{12}$ to Vitamin $B_{12r}$ can be accomplished by conventional techniques. For example, Vitamin $B_{12r}$ may be formed by exposure of the Vitamin $B_{12}$ compound in aqueous solution to hydrogen in the presence of platinum oxide catalyst.

The Vitamin $B_{12r}$ and radioactive isotope dopant are then mixed in aqueous solution to form a reaction solution. This reaction solution is then freeze-dried, likewise by conventional methods. Typically, this comprises freezing liquid material, usually using liquid nitrogen, and subsequently subjecting the material to a continuous vacuum. The result of the freeze-drying step is to provide a dry solid reaction mixture. It is to be understood that any other method of removing solvent from solution to provide an essentially dry solid reaction mixture may be substituted for freeze-drying in accordance with the invention.

The solid reaction mixture is thereafter exposed to an electron-accepting gas, such as oxygen, and then subjected, in the presence of the electron-accepting gas, to thermal treatment comprising maintenance of the solid mixture at a temperature of between 100°–300°C for a period of approximately 24–96 hours. As a result, isotopic exchange between the radioactive cobalt isotope dopant and the Vitamin $B_{12r}$ occurs, thereby producing Vitamin $B_{12r}$ labeled with the radioactive cobalt isotope dopant.

It has been found desirable in some instances to include an additional optional step after the thermal treatment of the reaction mixture, so as to increase the yield of the isotopic exchange. In accordance therewith the reaction mixture is exposed to an atmosphere of high relative humidity, usually about 95%, for a period of at least 24 hours.

Finally, the labeled Vitamin $B_{12r}$ may be converted to a higher redox state, that is it may be converted to labeled Vitamin $B_{12}$. This may be accomplished by any number of conventional techniques, depending on the specific complex cobalt chelate involved. For example, in the case of labeled Vitamin $B_{12r}$, the reaction mixture is dissolved in water to which a trace amount, for example, 1–2mg, of cobalt chloride hexahydrate is added and thereafter passed through an ion exchange or chelating resin to produce an effluent containing a purified labeled aquocobalamin containing the radioactive cobalt isotope. Potassium cyanide is then added to the purified labeled aquocobalamin to form dicyanocobalamin, which, when the pH of the solution is adjusted to about 4.0, will produce the labeled Vitamin $B_{12}$ containing the radioactive isotope of cobalt.

The details of this method of synthesizing labeled Vitamin $B_{12}$ are hereinafter set forth by way of example.

EXAMPLE 1

The synthesis of Vitamin $B_{12}$ containing $^{57}Co$ (III) is accomplished in five stages; reduction of Vitamin $B_{12}$ to Vitamin $B_{12r}$, formation of a solid state reaction mixture comprising Vitamin $B_{12r}$ and $^{57}Co^{+2}$ dopant, increasing the defects in Vitamin $B_{12r}$ by exposure to an electron-accepting gas, activation of the $^{57}Co^{+2}$ by treatment until isotopic exchange is substantially complete and conversion of the Vitamin $B_{12r}$ containing $^{57}Co$ (II) to Vitamin $B_{12}$ containing $^{57}Co$ (III).

The reduction of Vitamin $B_{12}$ to Vitamin $B_{12r}$ was accomplished as follows: 10 mg of $PtO_2$ catalyst was suspended in 8 ml of distilled, deionized water and, thereafter placed in a sealed glass vial, which was adapted for bubbling gas therethrough. Hydrogen gas was allowed to bubble through the solution for about 20 minutes, whereafter the seal was broken and 8 mg of Vitamin $B_{12}$ was quickly added to the vial, which was again resealed. Hydrogen gas was again passed through the solution for an additional 20 minutes and a dark brown solution of Vitamin $B_{12r}$ was produced.

To prepare the reaction mixture of Vitamin $B_{12r}$ and $^{57}Co^{+2}$ dopant, 1 mc (millicurie) of $^{57}CoCl_2$ was added to 1 ml of the Vitamin $B_{12r}$ solution (containing 1 mg of Vitamin $B_{12r}$), in a nitrogen atmosphere. This solution was gently mixed and thereafter freeze-dried in a continuous vacuum to form a solid reaction mixture.

This solid reaction mixture was then immediately exposed to a pure dry oxygen atmosphere at a pressure of between about 40–200 mm Hg., whereby the electron-accepting defects are formed on the surface of the Vitamin $B_{12r}$.

The solid mixture in the oxygen atmosphere was then subjected to a thermal treatment comprising maintenance of a temperature of about 150°C for 24 hours, whereby isotopic exchange was induced through activation of the $^{57}Co^{+2}$ by freed "holes". The yield of isotopic exchange upon completion of the thermal treatment was greater than 50%.

The reacted solid mixture was then dissolved in distilled water, to which about 1–2 mg of cobalt chloride hexahydrate was added, and purified by passage through a column containing Dowex A-1 Chelating resin (50–100 mesh). The resulting solution contained labeled aquocobalamin, a derivative of cyanocobalamin wherein the cyanide group is replaced by $H_2O$, and was free of Cobalt (+2) ions. The labeled aquocobalamin was then converted to labelled cyanocobalamin by addition of 4 mg of potassium cyanide to the solution. A purple color resulted, indicating the formation of dicyanocobalamin. The solution was then acidified to pH 4.0, by addition of dilute hydrochloric acid, with care being taken to provide adequate ventilation since toxic hydrogen cyanide gas was released as the dicyanocobalamin was converted to cyanocobalamin. The solution was then freeze-dried to remove excess hydrochloric acid, then redissolved in distilled water and desalinized using Dow Osmolyser. The resuling solution was again freeze-dried to provide Vitamin $B_{12}$ labeled with $^{57}Co$ (III) having a specific activity of about 1 mc/mg.

EXAMPLE 2

Vitamin $B_{12}$ labeled with $^{57}Co$ (III) was prepared following a procedure similar to Example 1, however, an additional step was included after the thermal treatment of the solid reaction mixture. After the thermal treatment was completed, the dry reaction mixture was placed in a hydration chamber having a relative humidity of about 95% and kept at 35°C for 24 hours. It was found that this additional optional step was effective in increasing the yield of isotopic exchange to better than 80%.

Thereafter, the reaction mixture containing labeled Vitamin $B_{12r}$ was purified and converted to labeled Vitamin $B_{12}$, in accordance with the procedure of example 1.

As will be readily apparent to one skilled in the art, various modification in the experimental techniques and choice of specific reactants including, but not limited to, the complex metal chelate compound, the radioactive metal isotope dopant, the electron-accepting gas, and solvents of high dielectric constant, may be made in the practice of the invention to provide labeled complex metal chelate compounds of various degrees of specific activity, all within the spirit and scope of the present invention as recited in the appended claims.

What I claim is:

1. A method of labeling a complex metal chelate compound with a radioactive metal isotope, comprising the steps of:
   a. providing a radioactive metal isotope dopant and a complex metal chelate compound in solution; then
   b. removing solvent from said solution of radioactive metal dopant and complex metal chelate compound, whereby a solid mixture of said radioactive metal isotope dopant and complex metal chelate compound is formed; then
   c. exposing said mixture to an electron-accepting gas; and then
   d. subjecting said mixture in the presence of said electron-accepting gas to thermal treatment, whereby isotopic exchange between said radioactive metal isotope dopant and said complex metal chelate compound occurs and said complex metal chelate compound labeled with said radioactive metal isotope is produced.

2. The method of claim 1, wherein said complex metal chelate compound is provided in a reduced redox state and wherein said method further includes the additional step of converting the reduced complex metal chelate compound labeled with said radioactive isotope to a higher redox state.

3. The method of claim 1, furthermore including the additional step after thermal treatment, said of exposing said mixture to an atmosphere of high relative humidity, whereby the yield of said isotopic exchange is increased.

4. The method of claim 3, wherein said mixture is exposed to said atmosphere of high relative humidity at a temperature of about 35°C for a period of about 24 hours.

5. The method of claim 3, wherein said high relative humidity is about 95%.

6. The method of claim 1, wherein said electron-accepting gas is selected from the group consisting of oxygen, nitrous oxide, carbon dioxide and sulfur hexafluoride.

7. The method of claim 1, wherein said thermal treatment consists essentially of heating said mixture to a temperature of between 100°–300°C for a period of between 24–96 hours.

8. The method of claim 7, wherein said temperature is 150°C and said period is 24 hours.

9. The method of claim 1, wherein said complex metal chelate compound is selected from the group consisting of cobaltocene, cyanocobalamin, aquocabalamin, porphyrins, and phthalocyanines.

10. The method of claim 1, wherein said radioactive metal isotope dopant is a radioactive cobalt isotope dopant.

11. The method of claim 10, wherein said radioactive isotope of cobalt is selected from the group consisting of $^{57}Co^{+2}$ and $^{60}Co^{+2}$.

12. The method of claim 10, wherein said reduced complex cobalt chelate compound is formed by exposure of said complex cobalt chelate compound to hydrogen in the presence of $PtO_2$ catalyst in aqueous solution.

13. The method of claim 10, including the additional step of purifying said reduced complex cobalt chelate compound labeled with said radioactive isotope of cobalt.

14. The method of claim 13, wherein said purifying step comprises the steps of:
   a. providing a solution of said labeled reduced cobalt chelate compound in water;
   b. adding a trace amount of cobalt chloride hexahydrate to said solution;
   c. passing the solution of step (b), above, through a column containing a suitable $Co^{+2}$ ion exchange resin; and d. withdrawing the effluent from said column, said effluent containing a purified derivative of said labeled cobalt chelate compound which is substantially free of Cobalt (+2) ions.

15. A method of synthesis of Vitamin $B_{12}$ containing a radioactive isotope of cobalt, comprising the steps of:
    a. providing an aqueous solution containing reduced Vitamin $B_{12}$ and a radioactive cobalt isotope dopant, said reduced Vitamin $B_{12}$ having cobalt in the Co (II) redox state and said radioactive cobalt isotope dopant existing in the Co (+2) redox state in said solution; then
    b. freeze-drying said aqueous solution, whereby a solid mixture of said reduced Vitamin $B_{12}$ and said radioactive cobalt isotope dopant is formed; then
    c. exposing said solid mixture to oxygen gas; then
    d. subjecting said solid mixture in the presence of said oxygen gas to thermal treatment, whereby isotopic exchange occurs between cobalt in said reduced Vitamin $B_{12}$ and said radioactive cobalt isotope dopant and reduced Vitamin $B_{12}$ labeled with said radioactive isotope of cobalt is produced; and then
    e. converting said reduced Vitamin $B_{12}$ labeled with said radioactive isotope of cobalt to a higher redox state, whereby Vitamin $B_{12}$ containing said radioactive isotope of cobalt is produced.

16. The method of claim 15, wherein said radioactive isotope of cobalt is selected from the group consisting of $^{57}Co^{+2}$ and $^{60}Co^{+2}$.

17. The method of claim 15, including the additional step after said thermal treatment, of exposing said solid mixture to an atmosphere of about 95% relative humidity at a temperature of about 35°C for at least 24 hours, whereby the yield of said isotopic exchange is increased.

18. The method of claim 15, wherein said reduced Vitamin $B_{12}$ is prepared from Vitamin $B_{12}$ by the steps of:
    a. providing a reducing solution containing water and $PtO_2$ catalyst;
    b. bubbling hydrogen gas through said reduced solution for at least 15 minutes; then
    c. adding said Vitamin $B_{12}$ to said reducing solution, whereby said Cobalt (III) in said Vitamin $B_{12}$ is reduced to the Cobalt (II) state and said reduced Vitamin $B_{12}$ is formed.

19. The method of claim 15, wherein said solid mixture is exposed to said oxygen at a pressure between about 40 to 200 mm Hg.

20. The method of claim 15, wherein said thermal treatment consists essentially of heating said solid mixture to a temperature of about 100°–300°C for a period of between 24–96 hours.

21. The method of claim 20, wherein said temperature is 150°C and said period is 24 hours.

22. The method of claim 15, furthermore including the additional step of purifying Vitamin $B_{12}$ containing said radioactive isotope of cobalt by the steps of;
    a. dissolving said Vitamin $B_{12}$ containing said radioactive isotope of cobalt in water, whereby a solution is formed; then
    b. adding 1–2 mg of cobalt chloride hexahydrate to said solution; then
    c. slowly passing said solution through an ionic exchange column, said column containing a suitable $Co^{+2}$ ion exchange resin; then
    d. withdrawing said effluent from said column, said effluent containing purified aquocobalamin containing said radioactive cobalt isotope; and then
    e. converting said purified aquocobalamin to said Vitamin $B_{12}$ containing said radioactive isotope of cobalt.

23. The method of claim 22, wherein said purified aquocobalamin is converted to said Vitamin $B_{12}$ containing said radioactive isotope of cobalt by the steps of;
    a. adding potassium cyanide to said effluent containing said purified aquocobalamin, whereby dicyanocobalamin is formed; and then
    b. adjusting the pH of said effluent containing said dicyanocobalamin to about pH 4.0, whereby Vitamin $B_{12}$ containing said radioactive isotope of cobalt is formed.

* * * * *